United States Patent [19]

Goudy, Jr.

[11] Patent Number: 4,816,145
[45] Date of Patent: Mar. 28, 1989

[54] LASER DISINFECTION OF FLUIDS

[75] Inventor: Paul R. Goudy, Jr., Milwaukee, Wis.

[73] Assignee: Autotrol Corporation, Milwaukee, Wis.

[21] Appl. No.: 796,168

[22] Filed: Dec. 30, 1985

Related U.S. Application Data

[62] Division of Ser. No. 571,228, Jan. 16, 1984, abandoned.

[51] Int. Cl.$^4$ .......................... C02F 1/32; G01N 21/01
[52] U.S. Cl. ........................... 210/96.1; 210/243;
204/DIG. 11; 250/435; 250/437; 422/186.3
[58] Field of Search ............... 210/745, 748, 754, 758,
210/760, 764, 96.1, 97, 192, 243; 422/22-24, 29,
32, 906, 106, 186.04, 186.3, 905; 204/302;
250/435, 437

[56] References Cited

U.S. PATENT DOCUMENTS

| | | | |
|---|---|---|---|
| 3,757,248 | 9/1973 | Small | 331/94.5 |
| 4,042,509 | 8/1977 | Bowen | 210/192 |
| 4,115,280 | 9/1978 | Pratt, Jr. | 250/527 |
| 4,204,956 | 5/1980 | Flatow | 210/192 X |
| 4,265,747 | 5/1981 | Copa et al. | 210/764 X |
| 4,273,660 | 6/1981 | Beitzel | 210/192 X |
| 4,274,970 | 6/1981 | Beitzel | 210/192 X |
| 4,400,270 | 8/1983 | Hillman | 210/103 |
| 4,704,527 | 11/1987 | Prodi | 250/435 X |
| 4,753,778 | 6/1988 | Hoffmann | 250/437 X |

OTHER PUBLICATIONS

"Scientific-American", vol. 228, No. 6, Jun. 1973, pp. 112-115.
"Scientific-American", vol. 230, No. 6, Jun. 1974, pp. 122-127.

Primary Examiner—Tom Wyse
Attorney, Agent, or Firm—Quarles & Brady

[57] ABSTRACT

The disinfection of water or other fluid is accomplished by passing a stream of the fluid through a laser beam which radiates light in the ultraviolet range. A gas pulsed laser is disclosed which produces a beam having a substantial width and depth and a measurable length, as measured in the direction of fluid flow. The laser is positioned out of contact with the stream but with its beam filling the cross-section of the stream of water which can flow through a flume or over a weir. Flow meters are provided which adjust the rate of pulsing of the laser, and therefore the intensity of the ultraviolet light, in relation to changes in flow. Sensors are also provided to adjust the intensity of the laser for changes in turbidity or organic content of the fluid. In one embodiment the fluid flows through a spiral tube which directs the fluid to and fro through the laser beam. In another embodiment, the length of the laser beam is adjusted by adjusting the distance between the laser beam source and a diverging lens. The laser beam may be reflected off of mirrored surfaces, and utilizes the scattering of the ultra-violet light produced by suspended particles in the fluid being treated.

16 Claims, 3 Drawing Sheets

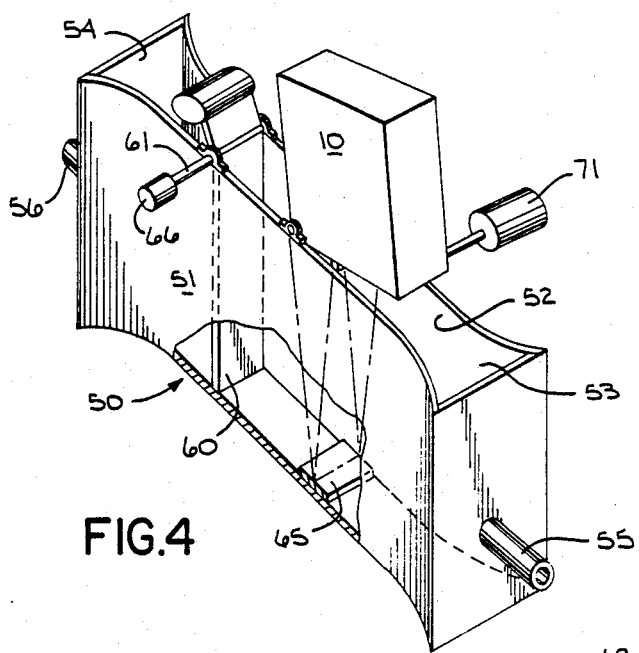
FIG.4
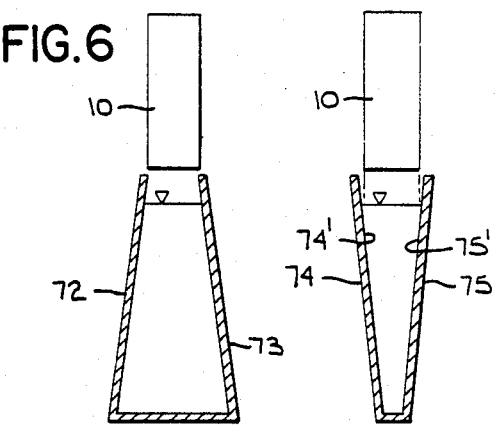
FIG.6
FIG.7
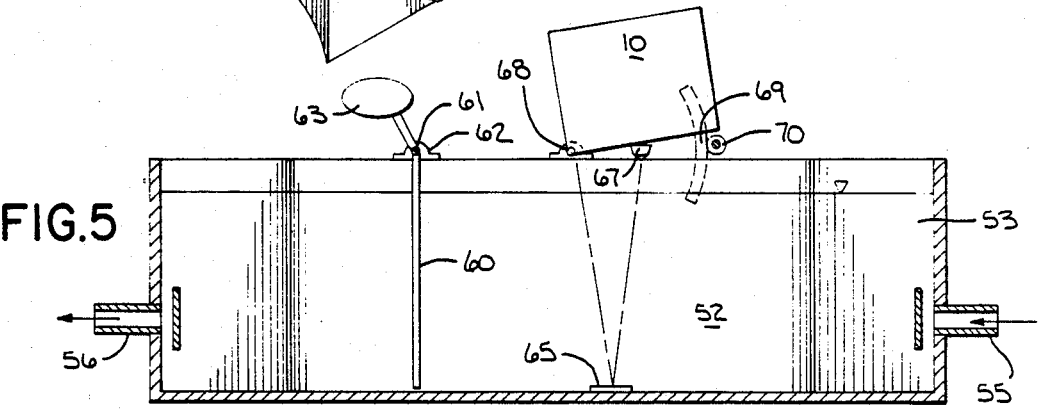
FIG.5
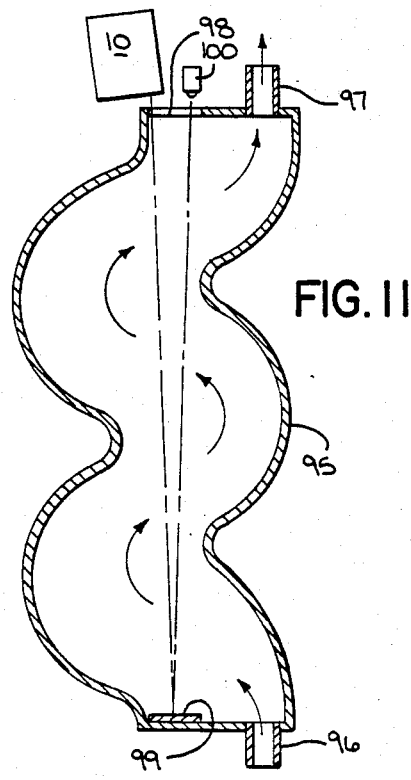
FIG.11
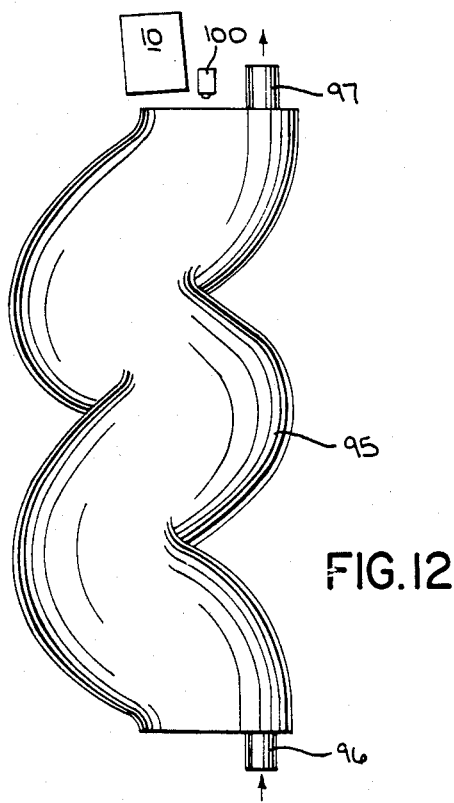
FIG.12

U.S. Patent  Mar. 28, 1989  Sheet 3 of 3  4,816,145
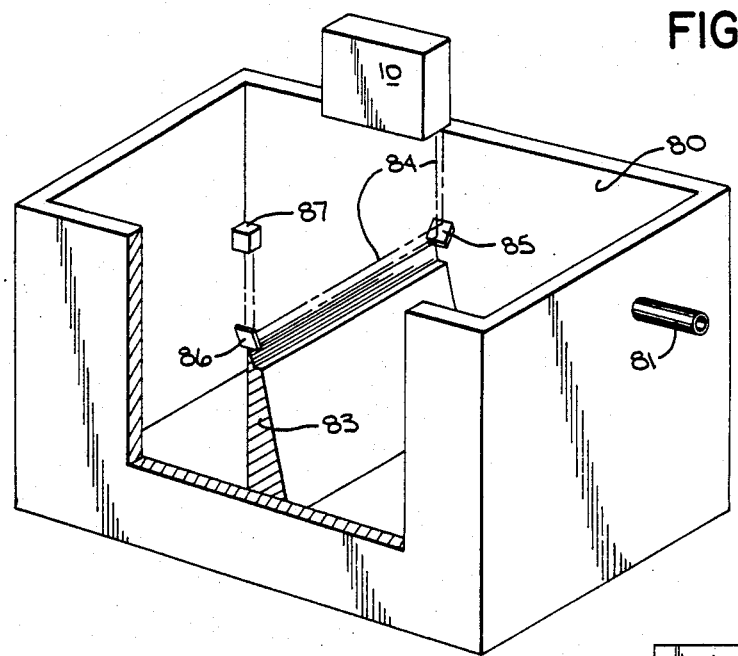
FIG. 8
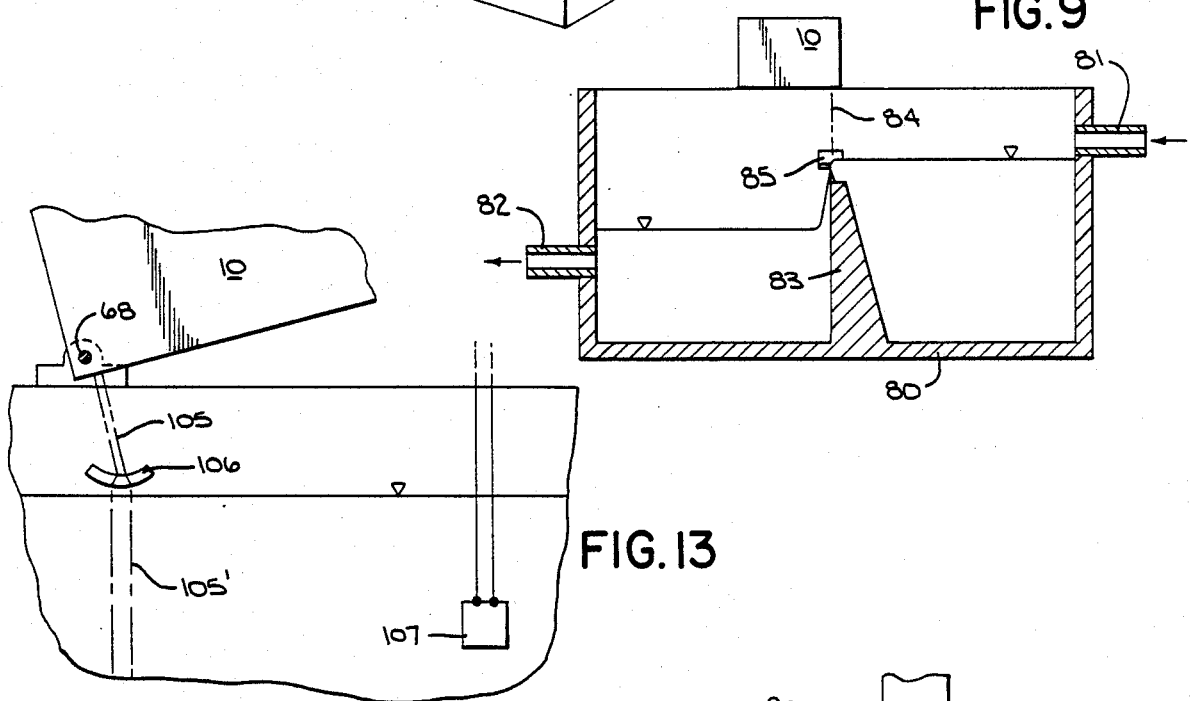
FIG. 9
FIG. 13
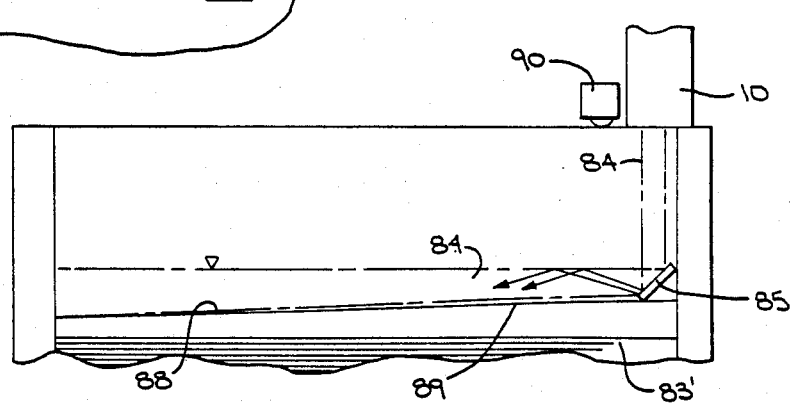
FIG. 10

LASER DISINFECTION OF FLUIDS

This is a divisional application of application Ser. No. 571,228, filed Jan. 16, 1984, abandoned.

BACKGROUND OF THE INVENTION

This invention relates to a method and apparatus for disinfecting water, and more particularly to such an apparatus and method which employ ultraviolet light generated by a laser.

Ultraviolet light is a known disinfection agent for water. It has been typical in the past to provide a series of banks of ultraviolet light bulbs and to flow the water to be treated over the surfaces of the bulbs. There are a number of disadvantages to this approach. First, the intensity of the ultraviolet light varies with the distance from the surface of the bulbs. Therefore, the bulbs must either be very closely spaced or special bulb arrays must be used which provide sufficient intensity of the ultraviolet light for all water flowing past the bulbs. Even then, the flow past the bulbs must be relatively slow so that an adequate dosage of the ultraviolet light is likely to result. The close spacing of the bulbs results in considerable head loss. Secondly, the bulbs have a tendency to become coated or clouded thereby reducing the intensity of the ultraviolet light. One approach to overcoming this problem has been to provide apparatus which allows for periodic removal and cleaning of the bulbs so as to minimize the loss due to coating. A second approach to the coating problem has been to provide an ultraviolet light intensity which is greater than initially needed so that the intensity will still be adequate even after the bulbs become coated. Thirdly, bacteria which are supported by suspended particles may not be exposed to the ultra-violet light if it is shielded from the light source by the particle.

There are sources of ultraviolet light in addition to the bulbs or lamps now commonly used for disinfection. One source is a laser which, by proper selection of the lasing gas, can be caused to radiate light in the ultraviolet range. The use of laser generated ultraviolet light has not been heretofore proposed for the disinfection of wastewater. The laser has decided operating advantages, including the ability to have its intensity, controlled in relation to operating conditions, such as flow rate, or characteristics of the water or other fluid being treated, such as turbidity or organic content. The geometry of the beam is also controllable to adjust for changing in operating conditions or fluid characteristics, The laser is capable of generating high intensity ultraviolet light and allows for faster velocities of the water, reduces head loss, will tolerate higher turbidity in the water and reduce the possibility of bacteria not being exposed to the ultraviolet light.

I have found ways in which to efficiently and effectively utilize the laser in the disinfection of water. By disinfection is meant the ability of a laser radiating in the ultra-violet spectrum to kill bacteria primarily by direct contact rather than by secondary photochemical effects. While these secondary effects might have the effect of killing the bacteria they can also lead to a reactivation of the bacteria which will have a negative effect on the disinfection process. Although my method and apparatus is particularly adapted for the treatment of water, it can also be employed to disinfect fluids generally, including those which are water based and those which are not, and including gases such as air.

SUMMARY OF THE INVENTION

In the broadest sense, my invention involves a method and apparatus for disinfecting a fluid which involves passing a stream of the fluid through a laser beam which radiates light in the ultraviolet range. My invention is particularly adapted for the disinfection of water and for the use of a gas pulsed laser whose rate of pulse and therefore average intensity of light can be adjusted. The pulse rate may vary from slow to so rapid as to be an essentially constant beam. The rate of pulse is adjusted for changes in the rate of flow of the stream of fluid passing through the laser beam and can also be adjusted for changes in the turbidity of water being treated so that the intensity of the ultraviolet light can be controlled to match that which is needed by conditions of operation or conditions of the fluid being treated.

Further in accordance with the invention I provide method and apparatus for varying the rate of flow of the stream of fluid while maintaining a constant intensity of the ultra-violet beam.

A laser beam in accordance with my invention has a substantial width and the stream is passed through the essentially stationary beam. The cross-section of the stream can be selected to correspond to the area of the beam or to take advantage of the effects of scattering of the light as the beam encounters suspended particles.

Still further in accordance with the invention I provide a method and apparatus for reflecting the beam off of a surface or surfaces of the container for the stream of fluid, or off of the surface of the stream itself. The reflection and scattering from the container surface is used to confine the spreading of the beam due to suspended particles in the fluid, and to decrease the beam cross-sectional area to compensate for alteration of the beam so as to maintain a nearly uniform intensity along the length of the region in which the beam and stream interact.

In one embodiment of the invention, I provide for adjustment of the angle of penetration of the beam with respect to the stream in response to changes in the turbidity of the fluid.

More particularly, in accordance with my invention I provide a method of disinfecting water which comprises the steps of providing a stream of water to be treated, generating a pulsed gas laser beam which radiates light in the ultraviolet range, and directing the laser beam into the stream of water. The method may include the additional steps of increasing the rate of the pulses of the laser bam in proportion to an increase in the rate of flow of water in the stream or in proportion to an increase in the turbidity of the water in the stream. The method preferably includes the step of sensing the amount of visible light scattered by suspended particles in the water as the method by which the rate of pulses of the laser beam is varied relative to changes in turbidity. The method may also include the step of altering the geometry of the laser beam, and particularly its length, in response to changes in fluid characteristics, such as organic content.

I also provide an apparatus for disinfecting water by th exposure of the water to light in the ultraviolet range which includes a water container having an inlet and an outlet, means for controlling the cross-section of the water flowing between the inlet and the outlet, and a pulsed gas laser having its beam filling the cross-section of the water and radiating light in the ultraviolet range.

The apparatus may also include means for sensing the visible light scattered by suspended particles in the water and for regulating the operation of the controlling means to reduce the cross-section of water as the amount of sensed visible light increases. The apparatus may also include means for controlling the rate of the pulses of the laser and flow responsive means in the container which regulate the operation of the pulse rate control, or means for sensing the visible light reflected by suspended particles in the water and for regulating the operation of the pulsed rate control in response to the amount of visible light. The apparatus may also include means for changing the length of the laser beam (as measured in the direction of fluid flow) in response to sensed change conditions of the fluid.

The container may take the form of a flume or a weir. In either event, the laser beam is directed transverse of the stream of water. The stream may be so shaped either by varying the width of the flume or the elevation of the weir that the cross-section of the stream matches the shape of the beam which diverges as it passes through the wastewater. The stream may also be so shaped that its cross-section narrows to compensate for alternation of the beam in turbid fluids.

It is a principal object of this invention to provide an effective and efficient method and apparatus for disinfecting water and other fluids by the use of ultraviolet light which does not involve contact with the fluid with the source of the ultra-violet light.

It is a further object of the invention to provide a method and apparatus for varying the ultraviolet light intensity of a source in response to operating conditions such as flow rate and in response to conditions of the water or fluid such as the turbidity.

It is yet another object of the invention to provide a gas pulsed laser apparatus which has provision for controlling the pulse rate of the laser in response to changes in turbidity or rate of flow of the stream of fluid being treated.

The foregoing and other objects and advantages will appear in the description which follows. In the following description of the preferred embodiments, reference is made to the attached drawings which form a part hereof.

BRIEF DESCRIPTION OF THE DRAWINGS

FIG. 4 is a view in perspective of a flume arrangement for disinfection of a fluid using the laser of FIGS. 1-3;

FIG. 5 is a view in longitudinal section of the flume of FIG. 4;

FIGS. 6 and 7 are cross-sectional views of alternate shapes of the flume of FIG. 5;

FIG. 8 is a view in perspective of a weir arrangement for the disinfection of wastewater using the laser of FIGS. 1-3;

FIG. 9 is a view in longitudinal section through the weir of FIG. 6;

FIG. 10 is a partial view in transverse section viewed along the weir but showing an alternate arrangement for the elevation of the weir;

FIG. 11 is a view in cross-section of a spiral tube container for treating a stream of wastewater by means of the laser of FIGS. 1-3;

FIG. 12 is a view in elevation of the spiral tube of FIG. 9.; and

FIG. 13 is a partial view in elevation of a modified form of the apparatus of FIGS. 4 and 5 which provides for adjusting the geometry of the laser beam.

DETAILED DESCRIPTION OF THE PREFERRED EMBODIMENT

Figure 1:
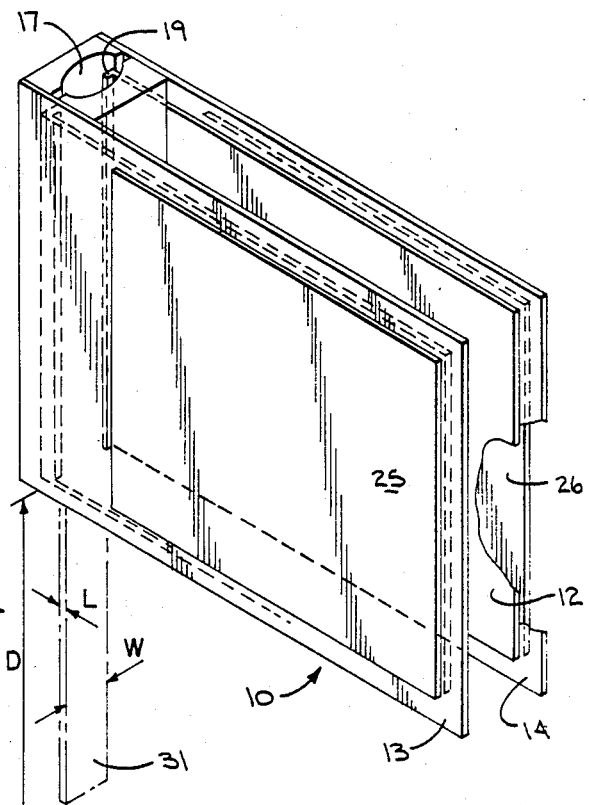
FIG. 1 is a view in perspective, with portions broken away for clarity, of a pulsed gas laser which is usable in the praactice of the invention.
Figure 2:
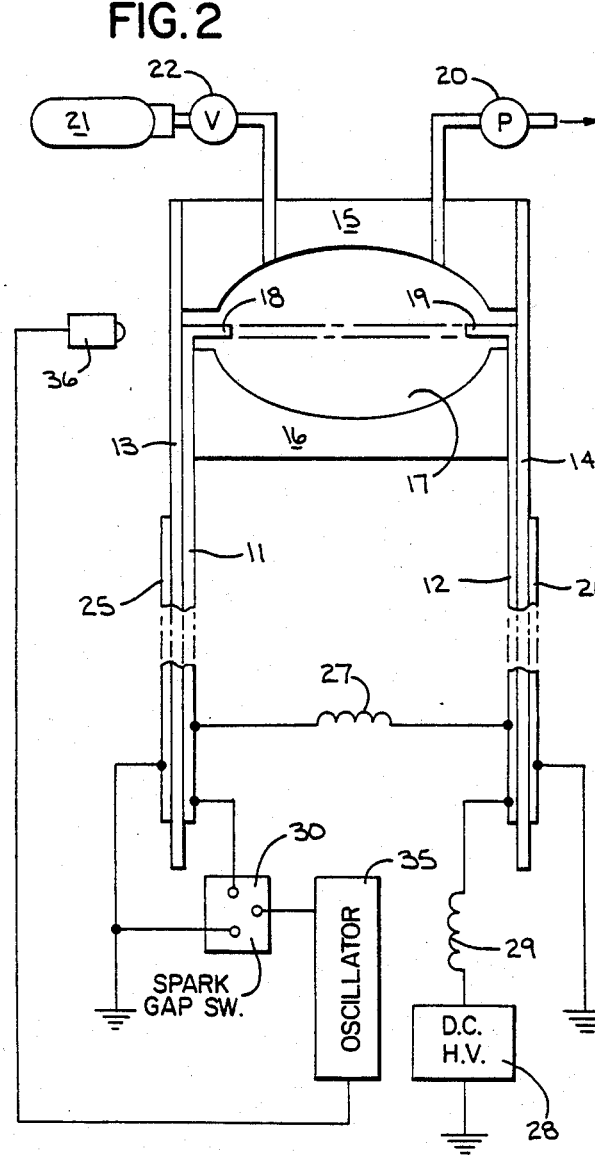
FIG. 2 is a top plan view, partially schematic, of the laser of FIG. 1.
Figure 3:
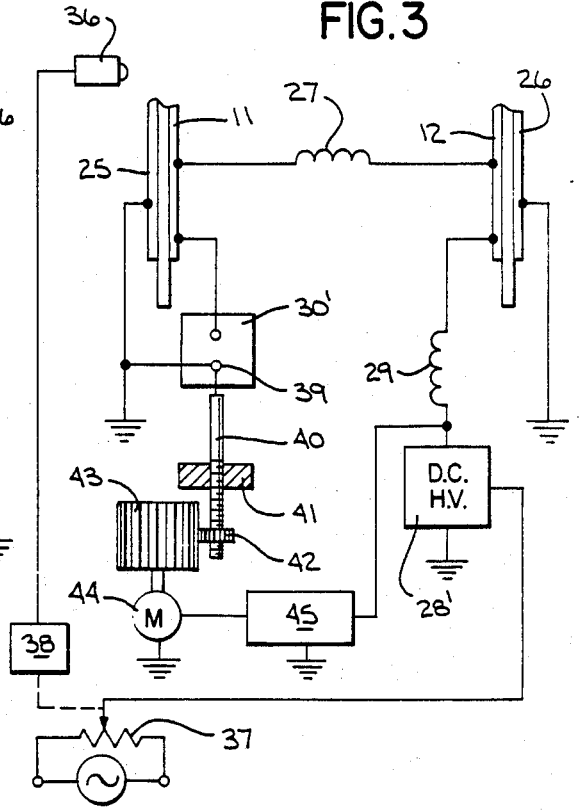
FIG. 3 is a partial view similar to FIG. 2 but showing alternate mechanisms and circuits for controlling the spark gap switch and voltage source.

Referring to FIGS. 1-3, a laser 10 is illustrated which is a modification of a pulsed gas laser of the type described in U.S. Pat. No. 3,757,248 issued Sept. 4, 1973 to Small for "Pulsed Gas Laser". The laser includes a pair of electrodes 11 and 12 each of which constitute one plate of a capacitor. The electrodes 11 and 12 are arranged on respective inner surfaces of a pair of dielectric plates 13 and 14, respectively, which are mounted parallel to each other and which are secured on opposite sides of a chamber assembly formed of chamber halves 15 and 16. The chamber halves 15 and 16 together define a chamber cavity 17 which is oval shaped and which extends longitudinally of the chamber assembly. The electrodes 11 and 12 are turned toward each other within the chamber 17 so that the respective electrode ends 18 and 19 confront each other and are spaced apart within the chamber 17. The chamber is connected to an evacuation pump 20 and is fed by a source of gas 21 which may be a pressure cylinder operating through a regulator valve 22.

A pair of conductive plates 25 and 26 are formed on the opposite, outside surfaces of the dielectric plates 13 and 14, respectively. Both of the conductive plates 25 and 26 are connected to ground. The electrode plates 11 and 12 are connected to each other through an induction coil 27 and the electrode plate 12 is connected to a high voltage d.c. source 28 through an induction coil 29. The high voltage d.c. source 28 will charge the electrode plate 12 and will thereafter charge the electrode plate 11 through the coil 27. A spark gap switch 30 is connected to the electrode plate 11 and will ground that plate periodically when the spark gap switch arcs. The sudden grounding of the electrode plate 11 will produce a very high potential across the gap between the electrode ends 18 and 19 such that electrons will flow between the ends. If the chamber is filled with a lasable gas such as nitrogen, the flow of electrons will cause lasing and a laser beam having a substantial width will result. The beam is illustrated in FIGS. 1 and 2 in phantom lines and is identified by the reference numeral 31. By the proper selection of the gas, the laser 10 will produce a beam 31 which radiates light in the ultraviolet range. Nitrogen is one such gas. The beam has a significant width (W) and a significant depth (D). The smallest dimension of the beam which will be called its length (L), is also measurable and can be manipulated to advantage, as will appear hereafter. The terms "length" is used because it is the dimension which describes the length of time that fluid will be exposed to the beam. The shape of the beam, that is one having a significant width, is in contrast with the typical laser beam which is a small diameter beam of light.

In a laser 10 usable in my invention, the exciting voltage produced by the high voltage source 28 may be in the magnitude of 30,000 volts with a gas pressure within the chamber 17 of 100 torr. This would produce a laser beam 31 which is about an inch wide and two feet in length.

The spark gap switch 30 can be periodically actuated to arc by use of an oscillator 35 in a known manner. In my invention, the rate of arcing of the spark gap switch and therefore the rate of pulsing of the laser 10 is adjusted for conditions of operation and conditions of the fluid being treated. That variation can result from the oscillator 35 being controlled by a photocell 36 which senses, as will be described in greater detail hereafter, the turbidity of the fluid being treated. An alternative arrangement for controlling the pulsing of the laser is shown in FIG. 3.

In FIG. 3, the high voltage d.c. rectifier 28' is connected to an a.c. source through a potentiometer 37 which is adjusted by an analog controller 38 in response to the amount of light sensed by the photocell 36. Changes in the amount of light sensed will therefor be reflected in changes in the amperage to the high voltage d.c. rectifier 28' and this will have the effect of adjusting the speed at which the plates 11 and 12 will be charged. Different charging speeds will produce different rates of pulsing the laser.

FIG. 3 also illustrates a mechanism to adjust the spark gap as the electrodes of the spark gap switch wear away. One contact 39 of the spark gap switch 30' is mounted on the end of a threaded rod 40 which is held in a threaded block 41 and which mounts a pinion gear 42. The pinion 42 meshes with a gear 43 mounted on the output shaft of the motor 44 which is controlled by a motor controller 45 responsive to the output voltage of the high voltage source 28'. As the spark gap increases due to electrode wear, the charging voltage to arc the spark gap will also increase. This is sensed by the motor controller 45 which causes the motor to move the contact 39 closer to the fixed contact to reduce the gap. Therefore, a predetermined charging voltage to the laser is maintained thereby insuring consistent laser pulses at discharge.

Referring to FIGS. 4 and 5, the laser 10 is shown mounted in relation to a flume structure indicated generally by the reference numeral 50. The flume 50 includes a container having a pair of upright side walls 51 and 52. The side walls are flared at both ends to form an inlet portion 53 and an outlet portion 54 communicating with respective inlet and outlet pipes 55 and 56. Between the flared ends, the side walls 51 and 52 are parallel and define an area of constant cross-section. Baffle plates 57 are disposed opposite the inlet and outlet pipes 55 and 56. A dam 60 fills the cross-section of the flume 50 and is mounted at its top on an axle 61 held in bearings 62 disposed on the opposite tops of the side walls 51 and 52. A counter weight 63 projects above the axle. The dam will control the flow of water through the flume and will be pivoted in the event of significant changes in the rate of flow. The dam 60 maintains the water depth in the flume and keeps the distance which the beam travels through the air to a minimum. The distance between the laser 10 and the surface of the water is exaggerated in the drawings. The laser 10 is mounted at the top of the flume 50 and has its laser beam projecting downwardly into the water passing through the flume. A mirrored surface 65 is disposed along the bottom of the flume and is arranged to reflect the laser beam.

The laser beam fills the constant cross-section of the flume 50 so that a stream of water flowing through the flume will be passed through the beam and all of the water will be exposed to the beam. The exposure to the ultraviolet light will disinfect the water by contact kill of the bacteria in the water. Since the total dosage of the ultraviolet light is important, the intensity of the laser beam is preferably adjusted to reflect the changes in the rate of flow of water passing through the beam. The intensity of the laser beam is controllable by adjusting the pulse rate of the laser. This can be accomplished by adjusting the oscillator 35 or the potentiometer 37.

In the embodiment of FIGS. 4 and 5, the dam 60 will respond to the flow of water through the flume and its angle relative to the vertical will change as flow changes. That is, the greater the flow the further the dam will be moved away from vertical. This change in position of the dam 60 is sensed by a resolver 66 which is connected to the axle 61 for the dam. The resolver 66 can then send a signal to the oscillator 35 or potentiometer 37 to thereby vary the rate at which the laser 10 is pulsed. For greater flow rate, the laser must be pulsed at a faster rate since there will be a reduction in the time of exposure to the laser beam.

Instead of the dam 60 and resolver 66, the flow rate may be sensed by the use of a known sonic depth meter which will measure the depth of water in the flume. The depth is proportional to the flow rate and the depth meter could be used to send a signal to the oscillator 35 or potentiometer 37.

I have determined that the efectiveness of the disinfection of a fluid, and particularly water, by the use of laser generated ultraviolet light is particularly sensitive to the turbidity of the fluid. It appears that suspended solids have the effect of reflecting and scattering the laser beam. Since the laser beam must penetrate a significant depth of the water, high turbidity will result in those portions of the water stream which are relatively remote from the entry point of the laser beam into the stream receiving low levels of ultraviolet light because the beam will have been significantly dispersed and scattered by the time it reaches the remote points. Thus, it is very desirable to increase the intensity of the laser beam whenever the turbidity increases. The increasing turbidity can be sensed by the use of a photoelectric cell sensor which, as illustrated in FIG. 5, is trained at the reflected laser beam and is responsive to the amount of light which is reflected back up toward the surface. The less the light, the greater the turbidity. Alternatively, a similar photoelectric cell can be trained simply at the surface of the water and can be responsive to the amount of visible light which is reflected and scattered by suspended particles in the water. In that case, the greater the amount of suspended solids, the greater will be the light sensed. In either case, the photoelectric cell is used to control the oscillator 35 or potentiometer 37 and thereby control the pulse rate of the laser 10.

Instead of adjusting the pulse rate as changes in turbidity are sensed, the angle of entry of the laser beam into the stream of water can also be adjusted in accordance with changes in turbidity. Thus, the laser 10 of FIG. 5 is mounted at one end on a pivot shaft 68 held in bearing blocks mounted on the tops of the side walls 51 and 52. A sector gear 69 is mounted on the laser 10 with its center of generation located at the pivot shaft 68. A pinion 70 engages the teeth of the sector gear 69 and the pinion is driven by a motor-reducer 17 responsive to signals from a photocell. For greater turbidity, the laser beam 10 would be automatically positioned by rotation of the pinion 70 in response to sensed light to a position in which the beam is more nearly vertical so that the beam reflected off the bottom will penetrate upwardly some distance and the area of least beam intensity will therefore be subjected to a double pass of the beam along the same path.

The embodiment of FIGS. 4 and 5 uses a separate flow meter in the form of a dam 60 and resolver 66 and a separate turbidity sensor in the form of the photocell 67. If the laser disinfection apparatus is installed as part of a larger waste-water treatment facility, which would typically be the case, the facility will have flow meters and turbidity meters used to control other portions of the treatment process. Those existing flow meters and turbidity meters can also be used to control the operation of the laser in accordance with this invention.

There are other conditions of the fluid being treated which can be sensed and can be used to control the intensity of the laser beam. For example, there are known Total Organic Carbon meters which give an instantaneous reading indicative of the organic content of the water or other fluid. The organic content may be related to the turbidity or the bacteria content. The instantaneous reading from the Total Organic Carbon meters can be converted into a signal which controls the pulse rate of the laser in the same manner as the photocell 67 or resolver 66 or other sensor of a condition or characteristic of the fluid.

In the arrangement of FIGS. 4 and 5, the side walls 51 and 52 of the flume are upright and are parallel at the narrowed center portion of the flume. In reality, the laser beam will have a tendency to become wider as it passes through the water being treated. If the intensity of the ultraviolet light is sufficiently high and the turbidity of the water or other fluid being treated is sufficiently low, the tendency of the beam to widen as it passes through the fluid can be used to advantage. Thus, as illustrated in FIG. 6, the flume may be formed with a central portion in which the side walls 72 and 73 are spaced wider apart at the base of the flume then at the top. A greater-cross-section can be achieved by that arrangement and therefore a greater quantity of water or other fluid can be treated per unit of time.

In very turbid wastewater, the intensity of the ultraviolet light is likely to be so diminished by scattering from the suspended particles that by the time it reaches the bottom of the stream it will have very little, if any, ability to kill bacteria. A container having a cross-section illustrated in FIG. 7 can be used to maximize the uniformity of the intensity of the ultra-violet light throughout the depth of the stream. In FIG. 7, the side walls 74 and 75 of the central portion of the flume are spaced closer together at the bottom of the flume than at the top thereby forming a Williamson cone. The scattering effect caused by the suspended particles will have a tendency in the arrangement of FIG. 7 to focus the beam towards the bottom. This tendency can be greatly enhanced by providing mirrored surfaces on all of the interior surfaces of the container. Thus, in the embodiment of FIG. 7 the surfaces 74' and 75' would be formed of a reflective material such as sheet aluminum as would the interior surface 76' of the base. The result will be that the laser beam will be reflected from the side surfaces and scattered by the suspended particles so that ultraviolet light of sufficient intensity to kill bacteria will reach the narrowed bottom of the flume.

All interior surfaces of all containers of each embodiment of this invention can also advantageously be provided with reflective surfaces to reflect the beam and take advantage of the scattering effect which will necessarily result from any suspended particles.

Referring now to FIGS. 8 and 9, the invention is shown incorporated into a weir structure which includes a box-like container 80 having an inlet pipe 81 and an outlet pipe 82 with an intermediate weir 83. The laser 10 is mounted on one side wall of the container 80 and has its laser beam 84 focused downwardly where it encounters an inclined mirror 85. The mirror reflects the beam along the upper edge of the weir 83. In the embodiment illustrated in FIGS. 6 and 7, the weir edge is horizontal and the beam is reflected by the mirror 85 in a path which is parallel to the horizontal top of the weir 83. A second mirror 86 may be positioned at the opposite end of the weir to reflect the laser beam to a photoelectric cell 87 for control of the pulse rate in relation to the amount of light sensed by the photocell 87.

It will be seen that in the embodiment of FIGS. 8 and 9, the cross-section of the stream of water which passes over the weir 83 will pass through the stationary reflected laser beam 84 so that all water passing between the inlet 81 and the outlet 82 will be exposed to the ultraviolet light.

In FIG. 10, a modification of the embodiment of FIGS. 8 and 9 is shown in which the elevation of the upper edge 88 of the weir 83' decreases as the distance from the mirror 85 increases. The result is a wedge-shaped cross-section of water passing over the weir 83'. This wedge-shaped cross-section of the stream is selected to coincide to the change which the laser beam 84 undergoes as it passes through the water. That is, the laser beam will tend to spread as it passes through the water. The modification of FIG. 10 also takes advantage of the phenomenon that the laser beam will be reflected back into the stream of water when it reaches the water surface if the angle of incidence at the meniscus exceeds the critical angle. This effect is illustrated by the arrow 89 in FIG. 10 which shows that the laser beam will be confined within the stream of water flowing over the weir 83'. A further modification of the weir design would narrow the cross-section of the water as the distance from the mirror increases by increasing the elevation of the upper edge of the weir as the distance from the mirror increases. This would be a similar effect to that of the embodiment of FIG. 7. The embodiment of FIG. 10 also uses a photoelectric cell 90 to sense the turbidity of the water and to adjust the pulse rate of the laser 10 in accordance therewith. Howver, unlike the photoelectric cell 87 in FIG. 8 which senses the light of the laser beam after it has passed through the water, the photoelectric cell 90 will sense the amount of scattered visible light reflected off of the suspended particles in the stream.

In the embodiments of FIGS. 4-7, and 8 and 9, the container is open to the environment. The container, whether it be the flume or weir, may advantageously be covered so as to exclude ambient light. Ambient light has the potential for including photoreactivation of the bacteria with the result that the bacteria will be reestablished rather than be killed.

Referring now to FIGS. 11 and 12, a further embodiment is illustrated which employs a spiral tube 95 having an inlet 96 at one end and an outlet 97 at its opposite end. Water entering the inlet will be forced to assume a spiral pattern as it passes to the outlet 97. A stationary laser 10 having its beam focused generally along the longitudinal axis of the pipe 95 is mounted adjacent the outlet end. The outlet end includes a transparent end wall 98 through which the beam can be focused. Inside the inlet end of the pipe 85 is a mirror surface 99 which will reflect the beam back upwardly and a photocell 100 is arranged near the laser 10 to sense the amount of visible light. Again, the embodiment of FIGS. 11 and 12 employ the principal of a stationary laser beam and a stream of water or other fluid being forced to pass the beam. However, in this embodiment, the stream will intersect the laser beam at multiple points along the length of the beam thereby increasing the exposure time of the water to the ultraviolet light.

All of the embodiments thus far described have means to adjust the intensity of the laser beam by adjusting the pulse rate. It is also possible to adjust the geometry of the beam to adapt it to changes in conditions or characteristics of the fluid. FIG. 13 shows an arrangement to accomplish a change in the beam geometry and particularly to vary the length (L) of the beam, that is, the smallest dimension. In the arrangement of FIG. 13, the laser 10 is mounted on a pivot 68 as in the embodiment of FIGS. 4 and 5. The angular position of the laser 10 is changed by the pinion 70 meshing with the sector gear 69. The laser beam 105 from the laser 10 is directed at a lens 106 which is a double concave diverging lens. The effect of the lens 106 will be to spread the length of the beam 105 so that the beam 105' will have an increased length. It is the increased length beam 105' through which the water passes as it is treated. The length of the beam 105' will be determined by the angle at which the beam 105' strikes the lens 106. That angle is adjusted by adjusting the relative angular position of the laser 10.

A sensor 107, such as a Total Organic Carbon meter, is disposed in the water being treated. The sensor 107 will produce a signal which is used to control the operation of the motor 71 and to change the angular position of the laser 10 as changes in the organic content of the water are sensed. As the organic content increases, the length of the beam 105' would be increased so that for a constant flow there would be a greater chance of exposure of bacteria to the ultraviolet light because of the increased resident time of the water passing through the beam 105'. A similar adjustment may be made for changes in turbidity. Even though the total photons will remain the same, the likelihood of contact of bacteria will increase especially if ther is turbulent flow as the water passes through the length of the beam 105'.

Reference has been made throughout to a gas pulsed laser as the preferred source for the ultraviolet light. By this term I mean to include those lasers which are commonly known as continuous lasers but which have such short intervals between their pulses and such a high pulse rate that they appear to be continuous. Such so-called continuous lasers do not allow for the degree of adjustment of intensity which the more typical lower pulse rate gas laser might have. However, they could be used with advantage in the embodiment of FIG. 13, for example, where the intensity of the laser beam is held constant and the beam geometry is altered in relation to operating conditions or fluid characteristics.

It will be noted that in each of the embodiments described above, the source of the laser beam is out of contact with the water or other fluid being treated. This is a significant advantage over the use of ultraviolet tubes or bulbs in which the water is typically passed over the tubes or bulbs. Since there is no contact between the laser beam source and the fluid, the laser source cannot become clouded or coated by impurities in the wastewater and there is no need to continuously clean the apparatus.

Although nitrogen will lase and produce light in the ultraviolet range, nitrogen is not the preferred gas to be employed in the laser of my invention. Based upon tests of a variety of eximers, it has been determined that the most efficient gas as measured by the amount of light per unit of power input into the laser is achieved by using an eximer of fluorine krypton. That eximer produces a wave length of 249 nanometers and tests have shown that it will exhibit about a 90% decrease in relative fecal coliform bacteria count at radiation doses of 0.15 joules per square centimeter and that a 99% or more decrease is achievable at doses of about 0.3 joules per square centimeter.

The use of the laser provides a superior source of intense ultraviolet radiation. As disclosed above, that source of radiation can be controlled, adjusted and varied to produce finite disinfection by the killing of bacteria. This is in contrast to the prior uses of ultraviolet radiation in which the radiation was simply provided in gross with the hope that the water or other fluid being treated would be exposed to sufficient radiation to be disinfected.

The flow of water through an apparatus in accordance with my invention can be considerably faster than that which was possible in the prior art arrangement using ultraviolet tubes or bulbs. As a result, the head loss is considerably reduced and the higher velocities tend to self-clean the surfaces of the container through which the fluid flows. This higher velocity will also cause suspended particles to tumble. The tumbling combined with the increased scattering of the ultraviolet light resulting from the greater intensity of the source and the reflection of the laser beam off of side walls or surfaces of the container, reduces the possibility that bacteria attached to suspended particles will not be exposed to the ultraviolet light. Instead, all sides of suspended particles should receive a dose of the ultraviolet light.

The use of a laser emitting light in the ultraviolet range permits the disinfection of fluids having a much higher turbidity than was possible using the tubes or bulbs involved of the prior approaches. In the method and apparatus of my invention, some turbidity may be desirable because of the scattering which will result. In prior apparatus, turbidity was always detrimental to successful operation. The present invention also provides for the adjustment of the pulse rate, the intensity, or the angle of the beam in relation to variations in turbidity.

I claim:

1. An apparatus for disinfecting water by the exposure of the water to light in the ultraviolet range, comprising:
    a water container having an inlet and an outlet;
    means including a flume for controlling the cross-section of water flowing between said inlet and outlet;
    a pulsed gas laser disposed above the flume and having its beam extending downwardly into the flume and filling the cross-section of the water, said beam being disposed between the inlet and outlet and radiating light in the ultraviolet range, said laser being mounted for pivotal movement on an axis transverse of said flume, whereby the path of said beam may be varied from the vertical; and means for sensing the turbidity of the water and for moving said laser to have the path of said beam move from the vertical as the turbidity of said water decreases.

2. An apparatus for disinfecting water by the exposure of the water to light in the ultraviolet range, comprising:

a water container having an inlet and an outlet;

means for controlling the cross-section of water flowing between said inlet and outlet;

a laser having a beam which has a width and depth substantially filling the cross-section of the water without reflection from the container, said beam being disposed between the inlet and outlet and radiating light in the ultraviolet range; and means for varying the length of said beam through which the water passes.

3. An apparatus in accordance with claim 2 wherein said means for varying the length of said beam includes a lens and means for changing the distance between the laser and the lens.

4. An apparatus for disinfecting water by the exposure of the water to light in the ultraviolet range, comprising:

a water container having an inlet and an outlet;

means for controlling the cross-section of water flowing between said inlet and outlet; and a pulsed gas laser having a beam with a substantial width, the beam filling the cross-section of the water with its width being generally transverse to the flow of water, said beam being disposed between the inlet and outlet and radiating light in the ultraviolet range.

5. An apparatus in accordance with claim 4 wherein said container is so shaped that said cross-section increases in width as the width of said beam increases as it passes through the water.

6. An apparatus in accordance with claim 4 wherein said container is so shaped that said cross-section decreases in width as the distance from the source of said beam increases.

7. An apparatus in accordance with claim 4 wherein said laser includes means for controlling the rate of the pulses thereof, together with flow responsive means in said container; said flow responsive means regulating the operation of said pulse rate control.

8. An apparatus in accordance with claim 4 wherein said laser includes means for controlling the rate of the pulses thereof, together with means for sensing the visible light reflected by suspended particles in said water and for regulating the operation of said pulse rate control in response to the amount of visible light.

9. An apparatus in accordance with claim 4 wherein said means for controlling the cross section of water includes a flume, said laser is disposed above said flume and said laser beam extends downwardly into the flume.

10. An apparatus in accordance with claim 9 together with a reflective surface at the bottom of said flume which is adapted to reflect the laser beam.

11. An apparatus in accordance with claim 10 wherein said laser beam extends downwardly at an angle to the vertical.

12. An apparatus in accordance with claim 4 wherein said means for controlling the cross-section of the water comprises a weir, and said beam extends generally parallel to the weir.

13. An apparatus in accordance with claim 12 wherein the elevation of said weir slopes downwardly away from the source of said laser beam so that the cross-section of water increases as the distance from said source increases.

14. An apparatus in accordance with claim 4 wherein said container contains reflective surfaces for reflecting light from said beam and light scattered from particles suspended in said water.

15. An apparatus in accordance with claim 4 wherein said container is closed to exclude ambient light.

16. An apparatus for disinfecting water by the exposure of the water to light in the ultraviolet range, comprising:

a water container having an inlet and an outlet;

means for controlling the cross-section of water flowing between said inlet and outlet;

a pulsed gas laser having its beam filling the cross-section of the water, said beam being disposed between the inlet and outlet and radiating light in the ultraviolet range; and means for sensing the visible light reflected by suspended particles in said water and for regulating the operation of said controlling means to reduce the cross-section of water as the amount of sensed visible light increases.

* * * * *